(12) United States Patent
Bariteau et al.

(10) Patent No.: US 11,963,675 B2
(45) Date of Patent: Apr. 23, 2024

(54) ORTHOPEDIC FIXATION DEVICES AND METHODS

(71) Applicant: Emory University, Atlanta, GA (US)

(72) Inventors: Jason Bariteau, Decatur, GA (US); Marissa McLaren, Pittsburgh, PA (US); John Joseph Watson, Houston, TX (US); Tyler Jenkins, Chesapeake, VA (US); Matthew Metzger, Auckland (NZ); Yuen Bak Ching, Atlanta, GA (US)

(73) Assignee: Emory University, Atlanta, GA (US)

( * ) Notice: Subject to any disclaimer, the term of this patent is extended or adjusted under 35 U.S.C. 154(b) by 265 days.

(21) Appl. No.: 16/936,332

(22) Filed: Jul. 22, 2020

(65) Prior Publication Data

US 2021/0022726 A1 Jan. 28, 2021

Related U.S. Application Data

(60) Provisional application No. 62/877,265, filed on Jul. 22, 2019.

(51) Int. Cl.
  *A61B 17/04* (2006.01)
  *A61F 2/08* (2006.01)
  *A61B 17/00* (2006.01)

(52) U.S. Cl.
  CPC ........ *A61B 17/0401* (2013.01); *A61F 2/0811* (2013.01); *A61B 2017/00004* (2013.01);
  (Continued)

(58) Field of Classification Search
  CPC ...... A61B 17/0401; A61B 2017/00004; A61B 2017/0404; A61B 2017/0409; A61B 2017/044; A61B 2017/0496; A61B 2017/0448; A61B 2017/0453; A61B 2017/0456; A61B 2017/0458; A61B 2017/0495; A61F 2/0811;
  (Continued)

(56) References Cited

U.S. PATENT DOCUMENTS 6,916,321 B2  7/2005  TenHuisen et al.
7,625,395 B2  12/2009 Mückter
(Continued)

OTHER PUBLICATIONS

Yerby, S A (A-DePuy), et al. ("The Effect of Cutting Flute Design on Bone Screw Insertion and Pull-Out Properties." 46th Annual Meeting. Orthopaedic Research Society. Orlando, Florida. Mar. 12-15, 2000. Poster Presentation https://www.ors.org/Transactions/46/0875.pdf).*

*Primary Examiner* — Katherine H Schwiker
*Assistant Examiner* — Nasheha Baset
(74) *Attorney, Agent, or Firm* — Emory Patent Group

(57) ABSTRACT

The devices and methods can provide short-term strength and rigidity and long-term stability and support after a bone and/or ligament injury in a single procedure. An orthopedic fixation device may include a body having a first end, a second end, and a length therebetween. The body may include a first portion, a second portion and a shaft portion disposed between the first portion and the second portion. The shaft portion may include one or more bioabsorbable materials. The body may include an internal channel disposed along the length. The device may also include a suture being disposed within the internal channel.

16 Claims, 10 Drawing Sheets

(52) U.S. Cl.
CPC ............... *A61B 2017/0404* (2013.01); *A61B 2017/0409* (2013.01); *A61B 2017/044* (2013.01); *A61B 2017/0496* (2013.01); *A61F 2002/0829* (2013.01); *A61F 2002/0852* (2013.01)

(58) Field of Classification Search
CPC ...... A61F 2002/0829; A61F 2002/0852; A61F 2220/0025; A61F 2220/0008; A61F 2220/0016; A61F 2210/0004; A61F 2002/30845; A61F 2002/3085; A61F 2002/30851; A61F 2002/30858; A61F 2002/30859; A61F 2002/30861; A61F 2002/30863; A61F 2002/30864; A61F 2002/30866; A61F 2002/30868; A61F 2002/30869; A61F 2002/30871; A61F 2002/30873
See application file for complete search history.

(56) References Cited

U.S. PATENT DOCUMENTS

| | | |
|---|---|---|
| 9,138,219 B2 | 9/2015 | Horrell et al. |
| 2007/0219557 A1* | 9/2007 | Bourque ............ A61B 17/0401 606/326 |
| 2007/0233123 A1* | 10/2007 | Ahmad ................ A61B 17/864 606/307 |
| 2008/0234762 A1 | 9/2008 | Forstein et al. |
| 2009/0043337 A1* | 2/2009 | Martin ............... A61B 17/0401 606/301 |
| 2013/0158597 A1* | 6/2013 | Hernandez ......... A61B 17/0401 606/232 |
| 2014/0243911 A1 | 8/2014 | Almarza et al. |
| 2016/0038201 A1 | 2/2016 | Cummings |
| 2019/0343507 A1* | 11/2019 | Chavan ............. A61B 17/0401 |

* cited by examiner

850

852

ORTHOPEDIC FIXATION DEVICES AND METHODS

CROSS-REFERENCE TO RELATED APPLICATIONS

This application claims the benefit of U.S. Provisional Application No. 62/877,265 filed Jul. 22, 2019. The entirety of this application is hereby incorporated by reference for all purposes.

BACKGROUND

High-ankle fractures often cause severe damage to the ligaments of the syndesmosis that fasten the tibia and fibula for ankle stability and controlled movement. When one of these ligaments is injured, the joint can be unstable as the syndesmosis prevents the lateral translation of the fibula. To repair the syndesmosis, traditionally, a titanium orthopedic screw has been used to temporarily fasten the tibia and fibula together at the ankle while the ligament heals. After 6-8 weeks, the screw is then removed with another procedure. This can not only drive up the medical costs but can create opportunity for more complications including infections. One alternative to a traditional orthopedic screw includes a flexible suture device that can be permanently implanted. However, the flexible suture devices can cause a soft tissue reaction that can require its removal. Also, the flexible suture devices do not provide the same short term structural support of an orthopedic screw that is ideal for healing immediately following surgery.

SUMMARY

Thus, there is a need for devices and methods that can provide both: 1) the short-term strength and rigidity of a screw and 2) the long-term stability and support of a suture without the need of a second procedure.

This disclosure is directed to devices and methods that can provide short-term strength and rigidity and long-term stability and support after a bone and/or ligament injury in a single procedure. This can improve patient outcomes while reducing the healthcare costs.

In some embodiments, the devices may include an orthopedic fixation device. The device may include a body having a first end, a second end, and a length therebetween. The body may include a first portion, a second portion and a shaft portion disposed between the first portion and the second portion. The shaft portion may include one or more bioabsorbable materials. The body may include an internal channel disposed along the length. The device may also include a suture being disposed within the internal channel.

In some embodiments, the methods may include a method of implanting an orthopedic fixation device into a target site of a patient. The method may include providing an orthopedic fixation device. The orthopedic fixation device may include a first portion, a second portion, and a shaft portion. The first portion may include a first instrument engagement member. The method may further include forming an opening in existing tissue in the patient. The method may include inserting an instrument into the first instrument engagement member. The method may further include using the instrument to insert the orthopedic fixation device through a hole formed in a first bone (e.g., tibia) and into a second bone (e.g., fibula) such that the first portion is anchored in the first bone and the second portion is anchored in the second bone with the shaft portion of the orthopedic fixation device being disposed between the first bone and the second bone.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
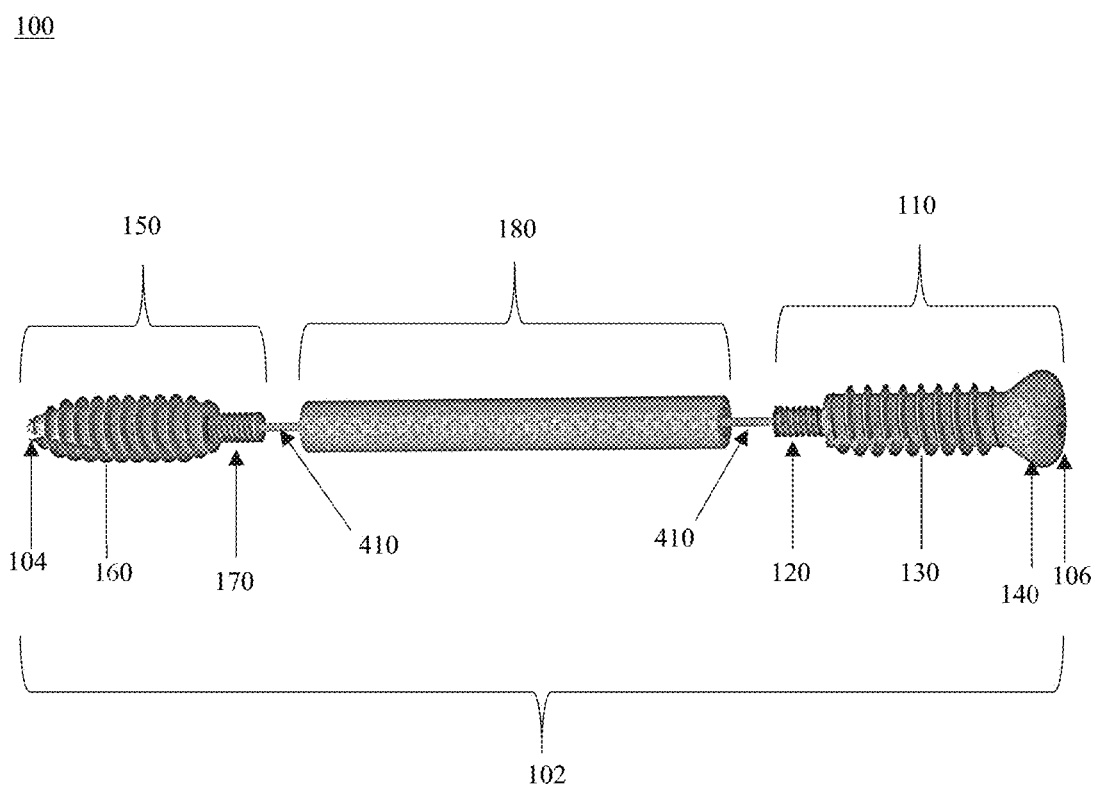
FIG. 1 shows an exploded, side view example of a device according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The devices and methods of the disclosure relate to orthopedic fixation devices and related methods for securing a bone, a joint and/or ligament, such as the ligaments of the syndesmosis. The devices can be customizable to fit the patient's anatomy. The devices and methods can provide both short-term and long-term stability in a single procedure.

In some embodiments, the devices may include portions that form a cannulated screw. The screw may include a head, tip and shaft portion disposed between the head and tip. The devices can be configured so that a suture can be contained within a channel running a length of the screw and secured within the head and tip of the screw. The shaft portion of the screw can be customized by a user (e.g., a clinician) to fit the patient's anatomy (e.g., the distance between the tibia and fibula) so that the head and tip of the screw can be anchored in the bones with the shaft extending between them. The suture may also be adjustable and customizable by a user (e.g., a clinician) to associate with the length of the shaft for each individual patient. This shaft portion may include one or more biodegradable or bioabsorbable materials that can be absorbed into the subject after an amount of time once the device has been implanted into the subject at the target site.

The devices can be implanted in a single procedure. After implantation, the shaft portion can be absorbed after a period of time and the head and tip portions of the screw can remain anchored in the bones and the suture can remain disposed therebetween, secured in the head and tip. The device of the disclosure can therefore provide initial rigid support after insertion into the patient for a period of time and then after absorption of the shaft portion, provide long-term flexible stability from the remaining head, tip, and suture.

The devices and methods of the disclosure are described with respect to a syndesmosis injury at the ankle. For example, the devices and methods can be configured to secure the tibia and fibula to allow the syndesmosis injury to heal. However, it will be understood that the devices and methods are not limited to this type of injury and/or ligaments. For example, the devices and methods can be configured to secure any ligament and/or bone region, such as to stabilize ligament/bone regions resulting from arm fractures, joint injuries, among others, or any combination thereof.

FIGS. 1-4B show an example of a device 100 according to some embodiments. In some embodiments, the device 100 may include a body 102 having a first end 104, a second end 106, and a length therebetween. In some embodiments, the body 102 may include one or more portions disposed along the length. For example, the body 102 may include a first portion 110, a second portion 150, and a shaft portion 180 disposed between the first portion 110 and the second portion 150.

In some embodiments, the first portion 110 and/or the second portion 150 may be removably attached to the shaft portion 180. In some embodiments, one or more of the first portion 110 and/or the second portion 150 may include a mating member complementary to a corresponding mating member of the shaft portion 180. In some embodiments, the first portion 110, the second portion 150, and the shaft portion 180 may be integrated into a single body.

In some embodiments, as shown in the figures, the first portion 110 may include a first end 112, a second end 114, and a length therebetween. In some embodiments, the first end 112 may be disposed within, surrounding, and/or adjacent to the shaft portion 180; and the second end 114 may be closest to the clinician.

In some embodiments, the first portion 110 may include one or more sections. In some embodiments, the one or more sections may be disposed adjacent and/or within each other. In some embodiments, the first portion 110 may include a first section 120, a second section 130, and a third section 140. The second section 130 may be disposed between the first section 120 and the third section 140.

In some embodiments, the first section 120 may be configured to be disposed within, surrounding, and/or adjacent to the shaft portion 180. In some embodiments, the first section 120 may include a mating member 122 configured to engage a complimentary, mating member 194 of the shaft portion 180. In some embodiments, the second section 130 may include a tissue engaging feature 132 disposed radially. In some embodiments, the third section 140 may include one or more instrument engaging members configured to engage an instrument and/or devices (e.g., ankle plates, suture tensioning devices, etc.). In some embodiments, the third section 140 may be configured to be partially disposed external to the target site and closest to the clinician.

In some embodiments, the second portion 150 may include a first end 152, a second end 154, and a length therebetween. In some embodiments, the second portion 150 may include a tip 156 at the first end 152 that may be configured to be disposed within and/or adjacent to the bone so as to be furthest from the clinician when inserting/implanting the device 100 at the target site. In some embodiments, the second end 154 may be disposed within, surrounding, and/or adjacent to the shaft portion 180.

In some embodiments the second portion 150 may include one or more sections. In some embodiments, the one or more sections may be disposed adjacent and/or within each other. In some embodiments, the second portion 150 may include a first section 160 and a second section 170.

Figure 2:
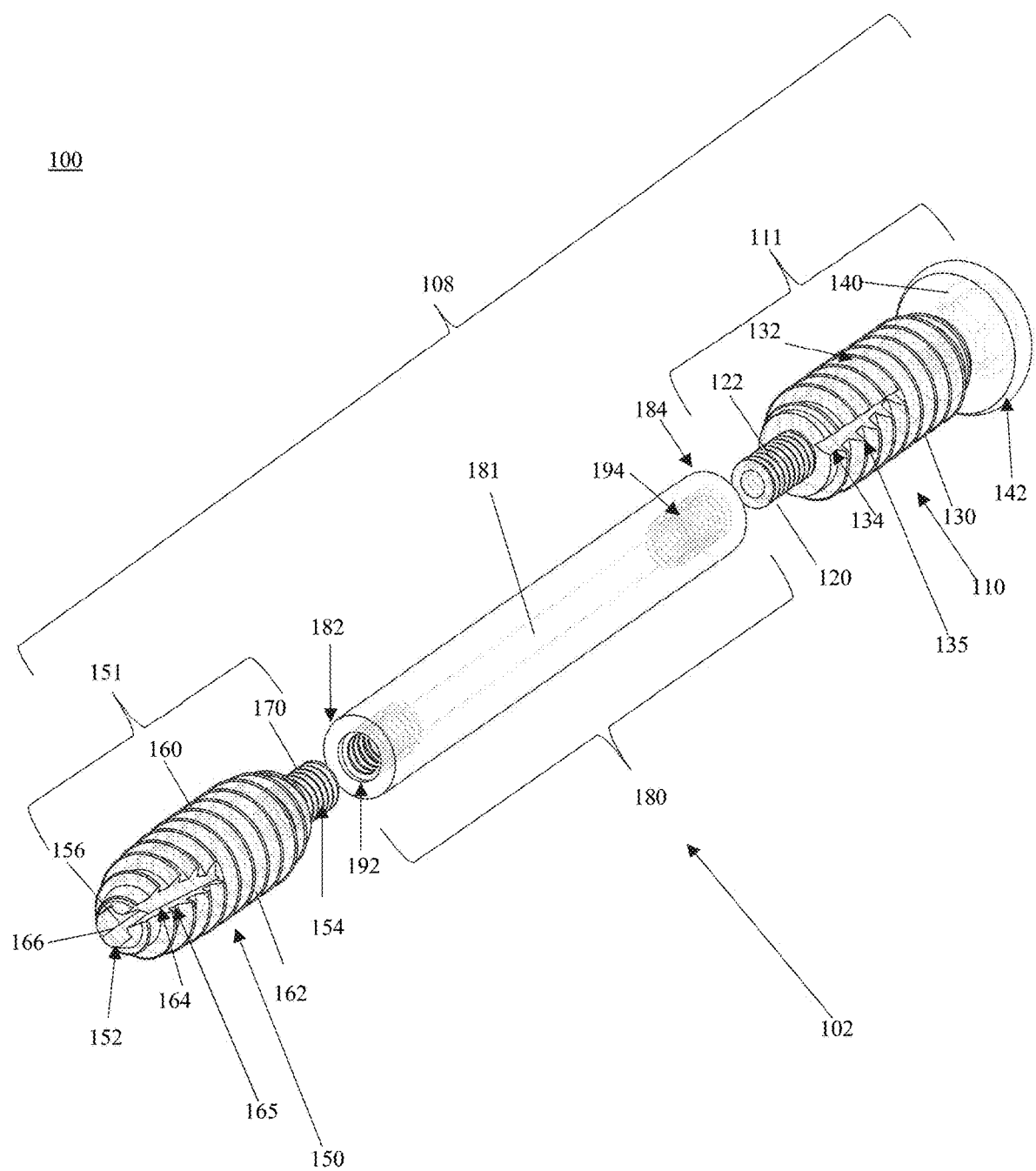
FIG. 2 shows an exploded, perspective view example of the device without an internal suture according to embodiments.

In some embodiments, the first section 160 may include the tip 156 and may be configured to be disposed closest to the target site and furthest from the clinician. The tip 156 may be open or closed. For example, as shown in FIG. 2, the tip 156 may be hollow and include an opening 166. In this example, the second portion 150 may include a channel 151 disposed along the length from the first end 152 (e.g., the opening 166) to the second end 154. In some embodiments, one or more sections of the second portion 150 may be solid. In some embodiments, the first section 160 may include one or more one or more instrument engaging members configured to engage an instrument and/or devices (e.g., ankle plates, suture tensioning devices, etc.).

In some embodiments, the second section 170 may be configured to be disposed within, surrounding, and/or adjacent to the shaft portion 180. In some embodiments, the second section 170 may include a mating member 172 configured to engage a complimentary, mating member 192 of the shaft portion 180.

In some embodiments, the first portion 110 and/or the second portion 150 may include one or more instrument engaging members disposed at one or more ends and configured to receive one or more instrument(s) for (i) implanting the device 100 and/or body 102 into a target area of a patient, (ii) removing the device, the body 102, and/or the respective portion from the target area of the patient, and/or (iii) adjusting the tension of a suture 410 disposed therein. The shape of the one or more instrument engaging members may be complimentary to the shape of the one or more instruments. For example, by including one or more instrument engaging members disposed on the first portion 110 and/or the second portion 150, these non-degradable/non-absorbable components of the body 102 can be more easily removed in case complications arise due to the implanted device 100, for example, if the target site becomes infected.

Figure 3A:
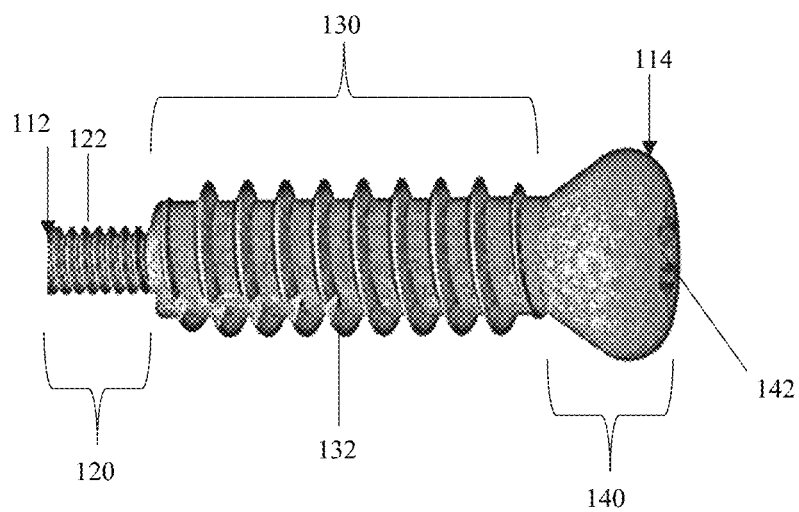
FIGS. 3A and 3B show a side view and perspective view, respectively, of the first portion of the device shown in FIGS. 1 and 2 according to embodiments.
Figure 3B:
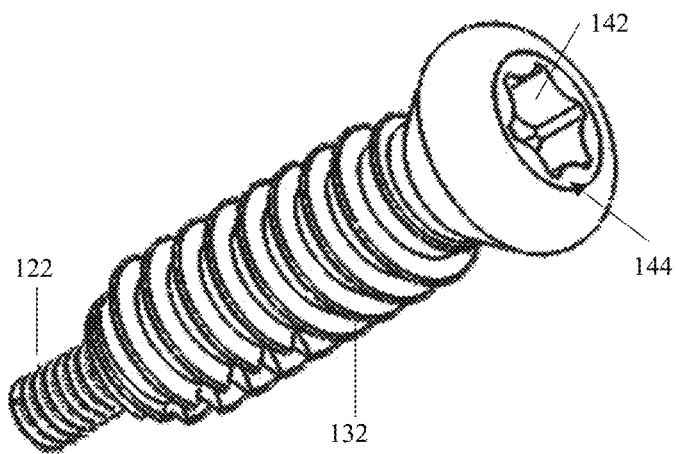

For example, as shown in FIG. 3A, the third section 140 of the first portion 110 may include one or more instrument engagement members 142 disposed at the end 112 and configured to receive an instrument(s), for example, for (i) implanting the device 100 and/or body 102 into a target area of a patient, (ii) removing the device, the body 102, and/or the first portion 110 from the target area of the patient, and/or (iii) adjusting the tension of the suture 410 disposed therein. In some embodiments, the one or more instrument engagement members 142 may include a first instrument engagement member 144. By way of example, the first instrument engagement member 144 may be a screw head configured to receive a complimentary screwdriver. In some embodiments, the first instrument engagement member 144 may further be configured to receive an instrument for removing the device 100 and/or one or more portions of the body 102 (e.g., the first portion 110) from the target site of the patient. In some embodiments, the third section 140 may include additional and/or alternative one or more instrument engaging members 142 configured to engage additional and/or alternative device(s), such as securing a plate (e.g., an ankle or other orthopedic plate) at the target site.

Figure 4A:
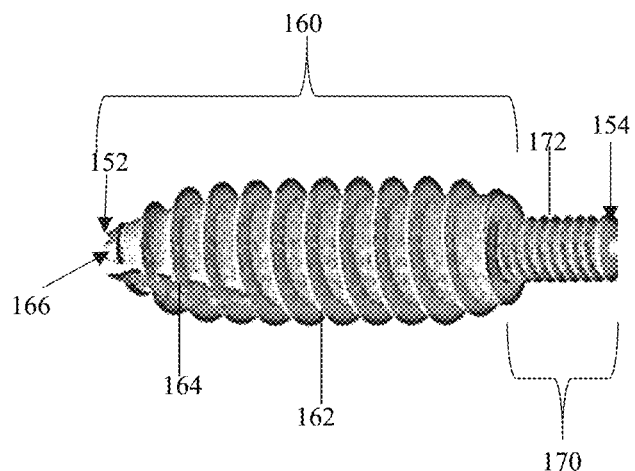
FIGS. 4A and 4B show a side view and a partial, perspective view, respectively, of the second portion of the device shown in FIGS. 1 and 2 according to embodiments.
Figure 4B:
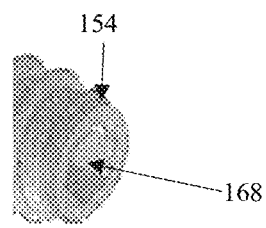

In some embodiments, the second portion 150 may include one or more instrument engaging members disposed at the first end 152 and/or the second end 154. The one or more instrument engaging members may be configured to receive an instrument for removing the device 100 and/or one or more portions of the body 102 (e.g., the first portion 110) from the target site of the patient. For example, as shown in FIG. 4B, the second portion 150 may include an instrument engaging member 168 disposed at the second end 154. In another example, the opening 166 disposed at the first end 152 may be also be an instrument engaging member. The shape of the instrument engaging member 168 is not limited to the hexagonal shape shown and may be any shape, for example, that is complimentary to the instrument structured to remove that portion and/or body.

In some embodiments, one or more of the portions 110 and/or 150 may include one or more tissue engaging features disposed along the respective surface. The tissue engaging features may be disposed along radially and/or linearly on the portions with respect to the body 102. In some embodiments, the one or more tissue engaging features may include thread(s), groove(s), depression(s), slot(s), other textured surface features, other surface features, among others, or a combination thereof.

In some embodiments, as shown in the figures, the first (head) portion 110 and the second (tip) portion 150 may each include one or more tissue engaging features configured to engage surrounding bone and/or tissue. As shown in the figures, the first portion 110 and the second portion 150 may include a (first) tissue engaging feature 132 and a (first) tissue engaging feature 162, respectively, disposed radially along the respective outer surfaces with respect to the body 102. In this example, the tissue engaging features 132 and 162 may be threads disposed radially. As shown in the figures, the tissue engaging feature 132 may be disposed along the second section 130 of the first portion 110 and the tissue engaging feature 162 may be disposed along the first section 160 of the second portion 150. The tissue engaging features 132 and 162 may be configured to engage a pre-drilled and/or pre-tapped hole at the target site. In some embodiments, the tissue engaging features 132 and 162 may be configured to help anchor the device 100 at the target site. For example, the tissue engaging features 132 and 162 may be suitable for cancellous and/or cortical bone anchoring.

In some embodiments, the first portion 110 and the second portion 150 may include an additional and/or alternative tissue engaging features. For example, as shown in the figures, the first portion 110 and the second portion 150 may further include a (second) tissue engaging feature 134 and a (second) tissue engaging feature 164, respectively. In this example, the tissue engaging features 134 and 164 may be slots disposed linearly along the respective outer surfaces with respect to the body 102 or perpendicularly with respect to a plurality of threads disposed on the respective outer surfaces. In some embodiments, each slot/tissue engaging feature 134, 164 may include a plurality of cutting ridges 135, 165, respectively, disposed on opposing sides of that slot. In some embodiments, each slot/tissue engaging feature 134, 164 may have a depth less than or equal to the depth of the respective thread on which each cutting ridge 135, 165, respectively, is formed.

As shown in the figures, the tissue engaging feature 134 may be disposed within the tissue engaging feature 132 and along the second section 130 of the first portion 110, and the tissue engaging feature 164 may be disposed within the tissue engaging feature 162 and along the first section 160 of the second portion 150. The tissue engaging features 134 and 164 may be configured to engage a pre-drilled and/or pre-tapped hole at the target site. The tissue engaging features 134 and 164 may be configured to assist in implanting the fixation device 100 by reducing torque on the patient's bone and the fixation device when the device 100 is implanted. This may be achieved by the tissue engaging features 134 and 164 creating threads in the pre-drilled and/or pre-tapped holes at the target site through which the device 100 is implanted. This created threads may then be engaged by the tissue engaging members 132 and 164 when the device 100 is implanted.

In some embodiments, the shaft portion 180 may include a first end 182, a second end 184, and a length therebetween. In some embodiments, the first end 182 may be disposed within or adjacent to the second portion 150. In some embodiments, the second end 184 may be disposed within or adjacent to the first portion 110.

In some embodiments, when the shaft portion 180 is configured to be removably attached to the first portion 110 and/or the second portion 150, the shaft portion 180 may include complimentary mating members disposed at the respective ends. As shown in the figures, the first portion 110 may include the mating member 122 disposed on the first section 120 and configured to mate with the complimentary mating member 194 disposed at the second end 184 of the shaft portion 180 so as to attach the first portion 110 to the shaft portion 180. In some embodiments, the mating member 122 may be a cylindrical extrusion with external threads complimentary to the mating member 194 and the mating member 194 may be an internal channel having threads complimentary to the mating member 122. For example, the mating member 122 may be a male screw and the mating member 194 may be a complimentary female screw.

In some embodiments, the second portion 150 may include the mating member 172 disposed on the second section 170 and configured to mate with the complimentary mating member 192 disposed at the first end 182 of the shaft portion 180 so as to attach the second portion 150 to the shaft portion 180. In some embodiments, the mating member 172 may be a cylindrical extrusion with external threads complimentary to the mating member 192 and the mating member 192 may be an internal channel having threads complimentary to the mating member 172. For example, the mating member 172 may be a male screw and the mating member 192 maybe a complimentary female screw.

In some embodiments, the body 102 may include an internal channel 108 disposed along the length. For example, the channel 108 may be disposed along the entire length of the shaft portion 180 (including channel 181 of the shaft portion 180) and between and/or within the first portion 110 (including channel 111 of the first portion 110) and/or the second portion 150 (including the channel 151 of the second portion 150). The channel 108 of the body 102 may be configured to receive one or more elongated coupling members or suture(s) (collectively referred to as "suture") 410. For example, the elongated coupling member(s) or suture(s) 410 may include one or more suture strands.

In some embodiments, the suture 410 may include any available bioabsorbable/biodegradable or nonabsorbable surgical suture. By way of example, the suture 410 may include one or more materials. By way of example, the suture 410 may be made of ultra-high molecular weight polyethylene (UHMWPE), polyester, nylon, or any other suitable material for long-term strength and flexibility in the subject formulated for surgical use, or any combination thereof. In some embodiments, the suture 410 may be a monofilament suture. In some embodiments, the suture 410 may include multiple sections. For example, the suture 410 may include multiple strands which may be twisted or braided together. In some embodiments the suture 410 may include an external sleeve or braided jacket enclosing the one or more internal strands.

In some embodiments, one or more portions of the body 102 may be made of titanium. In some embodiments the first portion 110 and the second portion 150 may be made of titanium. In some embodiments, the titanium material may allow for detection be a medical imaging modality, such as x-ray.

In some embodiments, the shaft portion 180 may be made of one or more biodegradable or bioabsorbable materials. For example, the shaft portion 180 may be made of magnesium alloy (AZ31). This way, the shaft portion 180 may be absorbed by the subject after an amount of time.

In some embodiments, the shaft portion 180 may include a surface coating. The surface coating may include one or more materials configured to increase/decrease the degradation/absorption rate of the shaft. For example, this coating may include PLLA 50/50 copolymer, DCPD, HA, FHA, or any combination thereof.

FIG. 1 shows an example of the device 100 with the suture 410 disposed within the channel 108 and along a length of the device 100 within the channel 108. In some embodiments the suture 410 may be a separate device that a user (e.g., a clinician) attaches to the orthopedic fixation device 100. In other embodiments, the suture 410 may be disposed into an integrated body 102 of the device 100.

In some embodiments, the device 100 may include one or more suture securing members configured to secure the suture 410 within or coupled to the device 100. For example, the first portion 110 and/or the second portion 150 may include one or more suture securing members disposed therein. In some embodiments, the suture securing member(s) may be within or adjacent to the respective internal channels 151, 111 of the second portion 150 and/or the first portion 110, respectively.

In some embodiments, the first portion 110 and/or the second portion 150 may include one or more suture securing members, for example, within respective channels 111, 151. For example, the opening 166 at the tip 156 may communicate with the internal channel 151 that is a part of the device channel 108. In some embodiments, the opening 166 may be configured to receive the suture 410. By way of example, a user (e.g., a clinician) may insert the suture 410 through the opening 166 of the tip 156 into the device channel 108 and a suture securing member may be disposed within the first section 160. In some embodiments, the suture securing member(s) may be adjacent to the tip 156. In some embodiments, the suture securing member(s) may be a screw interface, a barbed/screw interface, molded interface, knot interface, among others, or any combination thereof.

In some embodiments, the device may include one or more suture tensioning members, for example, in the first portion 110 and/or the second portion 150. For example, the suture tensioning member (s) may be configured to allow a user (e.g., a clinician) to adjust the tension of the suture 410 disposed within the channel 108, using the one or more instrument engaging members disposed at the respective end when and/or after the device 100 is implanted, for example, during and/or after surgery to implant the device 100. In some embodiments, the suture tensioning members(s) may be a screw-in-screw tensioning interface, an affixed suture interface, a looped/threaded suture interface, a barbed/screw interface, among others, or any combination thereof. In some embodiments, the one or more suture securing member(s) may also correspond to the one or more suture tensioning member(s).

Figure 5:
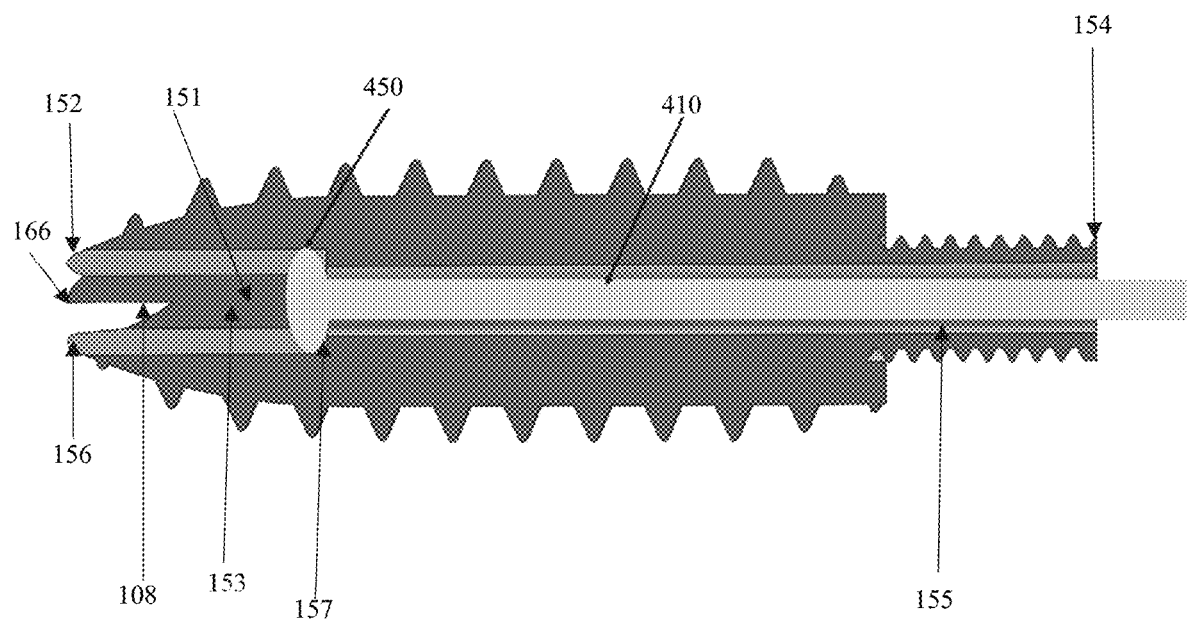
FIG. 5 shows an example of a suture securing member disposed in the second portion of the device according to embodiments.

FIG. 5 shows an example 500 of a suture securing member disposed in the second portion 150, according to some embodiments. As shown in this example, the suture securing member may be a suture interface that can be permanently molded during the manufacturing process or assembled by the clinician. As shown in FIG. 5, the channel 151 may extend along the length of the second portion 150 and be a part of the channel 108. The channel 151 may have a first diameter 153 that extends from the first end 152/tip 156/opening 166 to an interface 157 and a second diameter 155 that is smaller than the first diameter 153 that extends from the interface 157 to the second end 154. In this example, the suture 410 may be disposed within the channel 151 and secured at the interface 157, for example, by a suture interface 450. For example, the suture interface 450 may be a knot. In some embodiments, the first portion 110 may include one or more suture tensioning members, for example, as shown and described in the example shown in FIGS. 6-8B, as well as other suture tensioning member(s), to adjust the tension of the suture 410 in this example.

Figure 6:
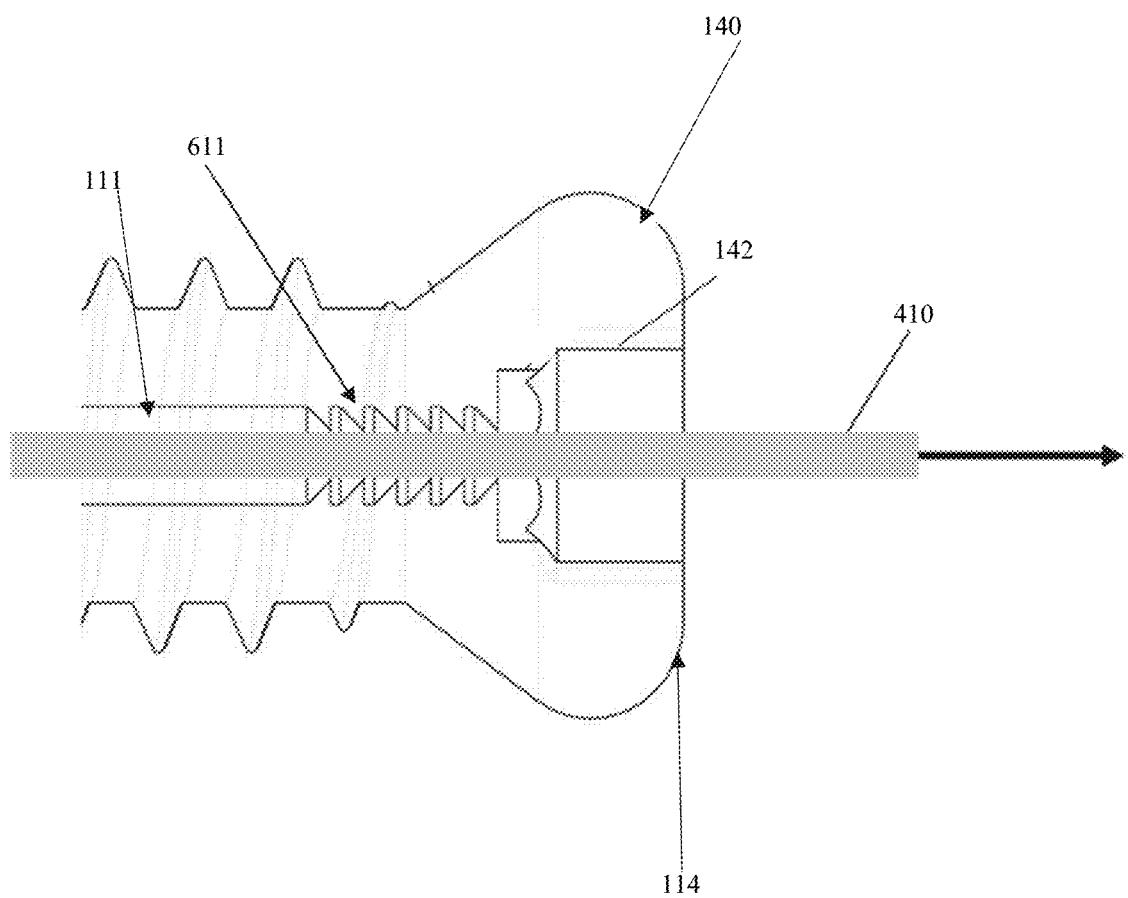
FIG. 6 shows an example a suture tensioning member disposed in the first portion of the device according to embodiments.

FIGS. 6-8B show examples of suture tensioning members disposed in the first portion 110, according to some embodiments. FIG. 6 shows an example 600 of a barbed interface according to some embodiments. As shown in FIG. 6, the first portion 110 may include a barbed interface 611 along the length of the inner channel 111. The barbed interface 611 may be disposed along the third section 140 and be configured to engage with the one or more instrument engaging members 142. The barbed interface 611 may include a disposed along its length. By way of example, the suture 410 may be threaded through the channel 108, 111 and through the barbed interface 611 and out of the second end 114. After the body is implanted, tension can be applied to the suture 410 by pulling on the suture 410. The barbed interface 611 can allow the suture to pass through easily in one direction (towards the direction of pulling) and can prevent it from moving in the opposite direction so that the suture could not slip back through the body 102 (e.g., the third section 140) once tensioned. In use, once the suture 410 is tensioned, the user can shorten the loose end of the suture 410 by cutting it, tying a knot, among others, or a combination thereof.

Figure 7A:
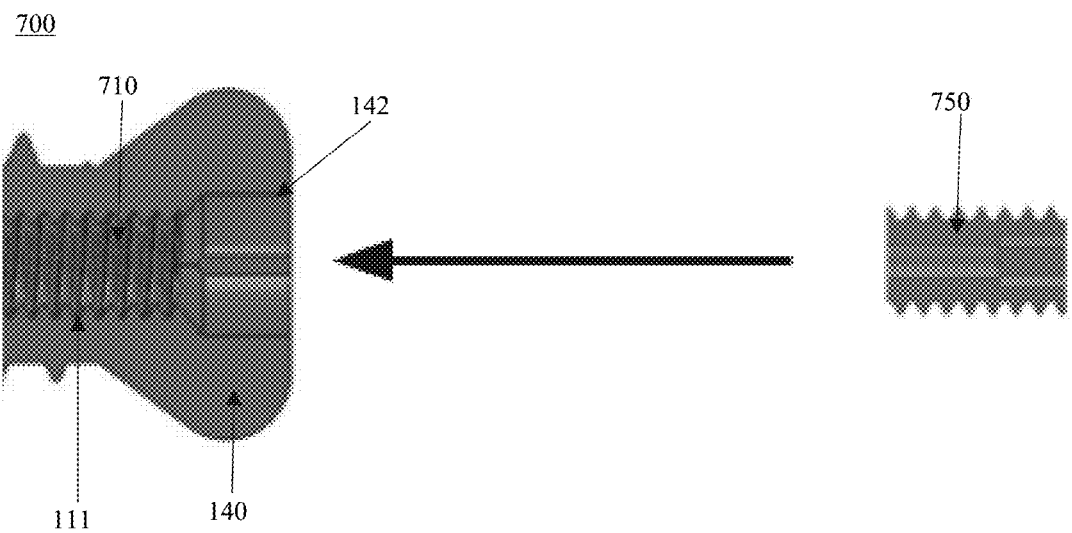
FIG. 7A shows another example of a suture tensioning member engaging the first portion of the device according to embodiments.
Figure 7B:
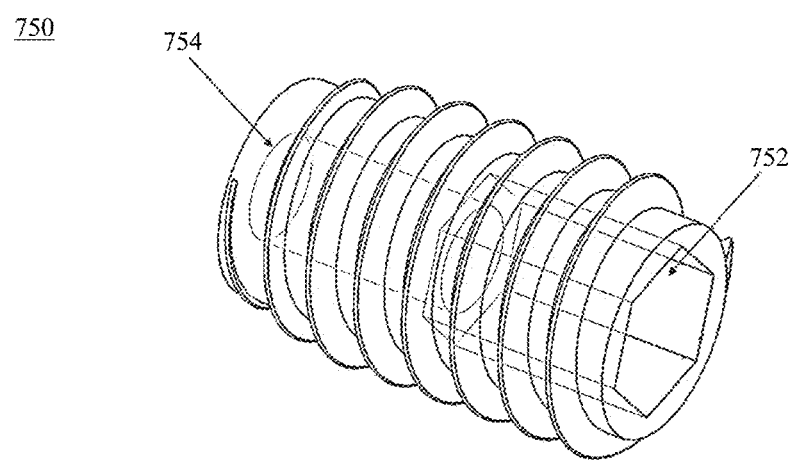
FIG. 7B shows an isolated view of the suture tensioning member of FIG. 7A according to embodiments.
Figure 7C:
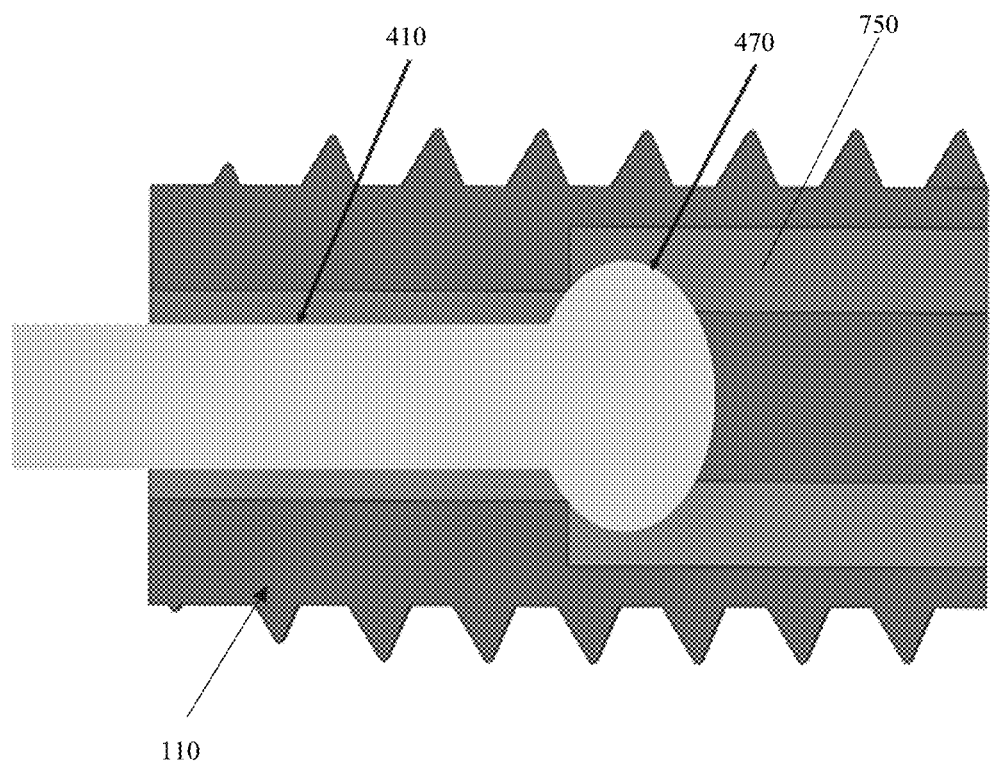
FIG. 7C shows the suture tensioning member disposed in the first portion of the device according to embodiments.

FIGS. 7A-C show an example 700 of a screw-in-screw tensioning interface according to some embodiments. As shown in FIG. 7A, a (screw) tensioning member 750, such as a hollow screw, may be driven into the first portion 110, for example, into the instrument engaging member 142, using an instrument, such as a surgical driving tool. The member 750 may be driven to engage the complimentary threaded member 710 disposed within the channel 111. As shown in FIG. 7B, the member 750 may include a hollow channel 754 disposed along its length and an instrument engaging member 752 for engaging the surgical driving tool. After the tensioning member 750 is inserted into the first portion 110, the suture 410 can be threaded through the channel 108 and secured within the tensioning member 750 using a knot 470, as shown in FIG. 7C. The tension of the suture can then be adjusted by rotating the tensioning member 750 using a surgical driver. For example, the suture can be tensioned by causing the tensioning member 750 to move towards the end 114 (e.g., clinician side) of the first portion 110 using a surgical driver.

Figure 8A:
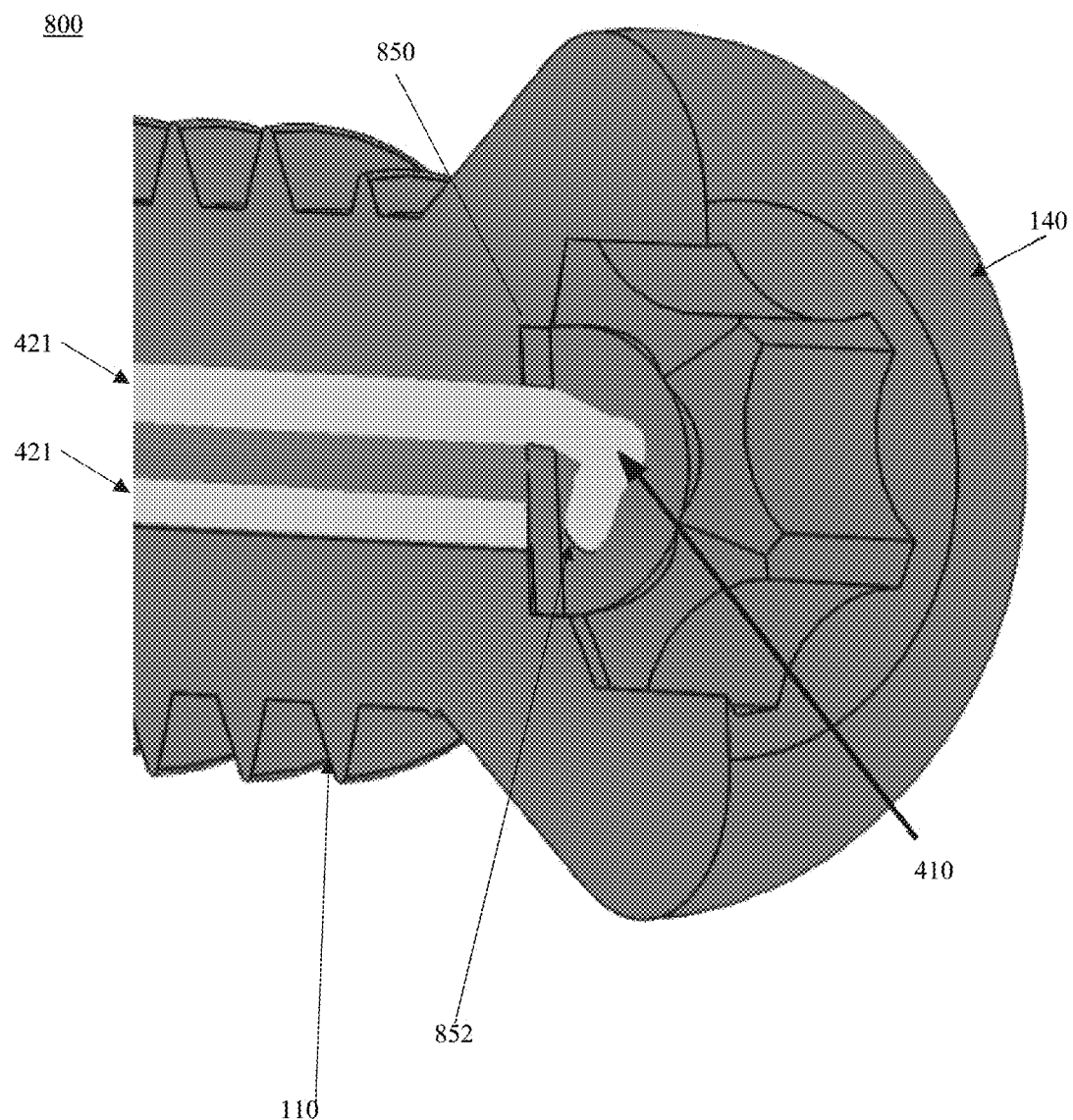
FIG. 8A shows another example of a suture tensioning member disposed in the first portion of the device according to embodiments.
Figure 8B:
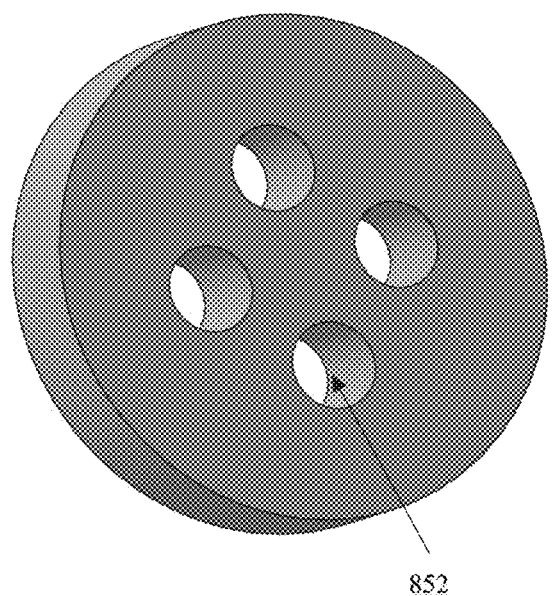
FIG. 8B shows an isolated view of the suture tensioning member of FIG. 8A according to embodiments.

FIGS. 8A and 8B show an example 800 of a looped/threaded suture interface according to some embodiments. As shown in FIG. 8A, a suture interface 850 may be disposed in the first portion 110. The suture interface 850 may be disposed in and/or adjacent to the section 140. The suture interface 850 may include one or more openings 852 in which the suture 410 may be threaded, as shown in FIG. 8B. The suture interface 850 is not limited to the circular plate shown and may be a different suture interface in which the suture 410 may be threaded. As shown in FIG. 8A, in use, the suture may through the opening(s) 852 of the plate so that the suture can be tightened by pulling on one of the suture lines 421 threaded through the interface 850, for example, using a complimentary feature disposed within the second portion 150 (e.g., the tip 156).

In some embodiments, one or more portions of the body 102 may be made of one or more materials. The one or more materials may include but is not limited to titanium. In some embodiments, the one or more materials of the first portion 110 and the second portion 150 may include titanium. In some embodiments, the titanium material may allow for detection be a medical imaging modality, such as x-ray.

In some embodiments, the shaft portion 180 may be made of one or more biodegradable or bioabsorbable materials. For example, the one or more materials may include magnesium alloy (AZ31). This way, the shaft portion 180 may be absorbed by the subject after an amount of time.

In some embodiments, one or more portions of the body 102 may include a surface coating. For example, the shaft portion 180 may include a surface coating that is configured to change the degradation/absorption rate of the shaft portion 180. For example, the surface coating may include one or more materials, such as PLLA 50/50 copolymer, DCPD, HA, FHA, among others, or any combination thereof.

In some embodiments, the devices and methods of the disclosure relate to a method of preparing an orthopedic fixation device. For example, the method may include evaluating bone function and position at an injury site to determine an initial position of a first bone in relation to a second bone and measuring the distance between the outer surface of the first bone to the outer surface of the second bone.

In some examples, the method may include adjusting the length of a shaft portion of the orthopedic fixation device to match the measured distance and incorporating the shaft portion into the body of an orthopedic fixation device. The method may further include fixedly attaching a suture, disposed within the internal channel of the device, to a first suture securing member disposed within the first portion of the orthopedic fixation device and to a second suture securing member disposed within the second portion of the orthopedic fixation device and adjusting the tension of the suture, by using the one or more suture tensioning members that are configured to receive one or more instruments at the one or more instrument engagement members, to correspond to the patient specific length of the shaft portion of the orthopedic fixation device.

In other examples, the orthopedic fixation device (the body 102 (e.g., the portions 110, 150 and/or 180)) may be pre-assembled with and/or without the suture 410. In this example, the method may include selecting the orthopedic fixation device from a plurality of different sized fixation devices having a size that corresponds to the measurement.

In some embodiments, the devices and methods of the disclosure relate to a method of implanting an orthopedic fixation device at a target site of a patient. For example, the method may include forming an opening in existing tissue in the patient, forming a hole at the target area through a first bone (e.g., tibia) and into a second bone (e.g., fibula). The method may further include inserting an instrument (e.g., a surgical screwdriver) into an instrument engagement channel and using the instrument to insert the orthopedic fixation device at the target area through the formed hole in the existing tissue in the subject and into the pre-drilled and/or pre-tapped hole at the target site in the first bone and into the pre-drilled and/or pre-tapped hole at the target site of the second bone such that first portion 110 of the orthopedic fixation device is anchored in the first bone and the second portion 150 of the orthopedic fixation device is anchored in the second bone with the shaft portion of the orthopedic fixation device being disposed between first portion 110 and the second portion 150.

In some embodiments, after the device is anchored, the device may remain permanently in the patient. The shaft portion of an orthopedic fixation device may be naturally absorbed into a patient after an amount of time leaving the suture 410 disposed between and anchored in the first portion 110 and second portion 150. This may allow for increased patient mobility at the site of the bone and/or ligament injury.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. An orthopedic fixation device, comprising:
   a body having a first end, a second end, and a length therebetween, the body including an internal channel disposed along the length;
   the body including a first portion, a second portion, and a shaft portion disposed between the first portion and the second portion;
   the first portion has a first end, a second end, and a length therebetween;
   the second portion has a first end, a second end, and a length therebetween;

the shaft portion including one or more bioabsorbable materials;

the shaft portion has a first end, a second end, and a length therebetween;

a section of the second portion being disposed within the shaft portion and adjacent to the first end of the shaft portion and a section of the first portion being disposed within the shaft portion and adjacent to the second end of the shaft portion;

the first portion including a mating member disposed at the first end and configured to mate with a complimentary mating member of the shaft portion, the section of the first portion including the mating member; and a suture being disposed within the internal channel.

2. The orthopedic fixation device according to claim 1, wherein:

the first portion includes an outer surface and the internal channel along the length of the first portion; and the first portion includes one or more tissue engaging features disposed along the outer surface, the one or more tissue engaging features including a plurality of threads disposed radially along the outer surface with respect to the length of the first portion.

3. The orthopedic fixation device according to claim 2, wherein the first portion includes:

an instrument engaging member disposed at the second end and configured to receive one or more instruments.

4. The orthopedic fixation device according to claim 3, wherein:

the second portion includes an outer surface and the internal channel along the length of the second portion;

the second portion includes one or more tissue engaging features disposed along the outer surface; and the one or more tissue engaging features includes a plurality of threads disposed radially along the outer surface with respect to the length of the second portion.

5. The orthopedic fixation device according to claim 4, wherein the second portion includes:

a tip disposed at the first end; and a mating member disposed at the first end and configured to mate with a complimentary mating portion of the shaft portion, the section of the second portion including the mating member.

6. The orthopedic fixation device according to claim 5, wherein the first end of the first portion is open or closed to the internal channel.

7. The orthopedic fixation device according to claim 5, wherein:

the shaft portion includes a first mating member disposed at the first end and a second mating member disposed at the second end;

the first mating member of the shaft portion is complimentary to and configured to mate with the mating member of the second portion; and the second mating member of the shaft portion is complimentary to and configured to mate with the mating member of the first portion.

8. The orthopedic fixation device according to claim 7, wherein:

the first mating member and the second mating member of the shaft portion are threaded female members disposed within the internal channel; and the mating member of the first portion and the mating member of the second portion are threaded male members complimentary to and configured to mate with the first mating member and the second mating member of the shaft portion, respectively.

9. The orthopedic fixation device according to claim 4, wherein:

the one or more tissue engaging features disposed along the first portion and/or the second portion includes a slot disposed perpendicularly to the plurality of threads and a plurality of cutting ridges disposed on opposing sides of the slot; and the slot has a depth less than or equal to a depth of plurality of threads on which the plurality of cutting ridges is formed.

10. The orthopedic fixation device according to claim 4, wherein the first portion and/or the second portion includes one or more suture securing members disposed within the internal channel of the first portion and/or the second portion and configured to couple to a portion of the suture disposed within the internal channel.

11. The orthopedic fixation device according to claim 10, wherein the one or more suture securing members includes one or more suture tensioning members configured to receive one or more instruments.

12. The orthopedic fixation device according to claim 11, wherein the one or more suture tensioning members includes a screw-in-screw tensioning device.

13. An orthopedic fixation device, comprising:

a body having a first end, a second end, and a length therebetween, the body including an internal channel disposed along the length;

the body including a first portion, a second portion and a shaft portion disposed between the first portion and the second portion;

the first portion has a first end, a second end, and a length therebetween;

the second portion has a first end, a second end, and a length therebetween;

the shaft portion including one or more bioabsorbable materials;

the shaft portion has a first end, a second end, and a length therebetween; and a section of the second portion being disposed within the shaft portion and adjacent to the first end of the shaft portion and a section of the first portion being disposed within the shaft portion and adjacent to the second end of the shaft portion;

each of the first portion and the second portion include a mating member disposed at an end of each portion and configured to mate with a complimentary mating portion of the shaft portion;

the section of the first portion includes the mating member of the first portion; and the section of the second portion includes the mating member of the second portion.

14. The orthopedic fixation device according to claim 13, wherein:

the first portion and/or the second portion includes one or more tissue engaging features disposed along an outer surface of each portion.

15. The orthopedic fixation device according to claim 14, wherein:

the shaft portion includes a first mating member disposed at the first end and a second mating member disposed at the second end;

each of the first mating member and the second mating member of the shaft portion is an internal channel with threaded female members;

the first mating member is complimentary to and configured to mate with the mating member of the first portion; and the second mating member is complimentary to and configured to mate with the mating member of the second portion.

16. The orthopedic fixation device according to claim 14, wherein:

a suture being disposed within and along the internal channel.

* * * * *